(12) United States Patent
Donskoy et al.

(10) Patent No.: US 6,801,131 B2
(45) Date of Patent: Oct. 5, 2004

(54) DEVICE AND METHOD FOR DETECTING INSECTS IN STRUCTURES

(75) Inventors: Dimitri Donskoy, Hoboken, NJ (US); Nikolay Sedunov, Hoboken, NJ (US)

(73) Assignee: Trustees of Stevens Institute of Technology

( * ) Notice: Subject to any disclaimer, the term of this patent is extended or adjusted under 35 U.S.C. 154(b) by 0 days.

(21) Appl. No.: 10/309,489

(22) Filed: Dec. 3, 2002

(65) Prior Publication Data

US 2003/0146840 A1 Aug. 7, 2003

Related U.S. Application Data

(63) Continuation-in-part of application No. 09/873,148, filed on Jun. 1, 2001, now abandoned.

(51) Int. Cl.[7] .............................................. G08B 23/00
(52) U.S. Cl. ..................... 340/573.1; 324/637; 324/639; 324/642
(58) Field of Search ............................. 340/573.1, 10.1, 340/545.3; 324/637, 639, 642; 119/721

(56) References Cited

U.S. PATENT DOCUMENTS

| | | | |
|---|---|---|---|
| 3,743,581 A | 7/1973 | Cady et al. ..................... 435/34 |
| 3,754,254 A | 8/1973 | Jinman ........................ 382/28 |
| 4,671,114 A | 6/1987 | Litzkow et al. ............... 73/587 |
| 4,809,554 A | 3/1989 | Shade et al. .................. 73/587 |
| 4,937,555 A | 6/1990 | Litzkow et al. ............. 340/540 |
| 4,941,356 A | 7/1990 | Pallaske ....................... 73/587 |
| 5,285,688 A | 2/1994 | Robbins et al. ............... 73/587 |
| 5,473,942 A | 12/1995 | Vick et al. ..................... 73/587 |
| 5,571,967 A | 11/1996 | Tanaka et al. ................ 73/587 |
| 5,575,106 A | 11/1996 | Martin et al. .............. 43/132.1 |
| 5,592,774 A | 1/1997 | Galyon ........................ 43/124 |
| 5,616,845 A * | 4/1997 | Hickling et al. .............. 73/584 |
| 5,815,090 A | 9/1998 | Su ........................ 340/870.16 |
| 5,877,422 A * | 3/1999 | Otomo ........................ 73/587 |
| 6,150,944 A * | 11/2000 | Martin et al. ............... 340/632 |
| 6,166,641 A | 12/2000 | Oguchi et al. ........... 340/573.1 |
| 6,255,652 B1 | 7/2001 | Moyer ........................ 250/343 |
| 6,313,643 B1 | 11/2001 | Tirkel et al. ................ 324/642 |

\* cited by examiner

Primary Examiner—Toan N. Pham
(74) Attorney, Agent, or Firm—McCarter & English, LLP (57) ABSTRACT

A device and method for detecting the presence of insects in a structure utilize a plurality of transceivers, each of which generates separate and distinct microwave signals and receives separate and distinct signals reflected from a structure being tested. The reflected signals received by each of the transceivers are processed, for instance by a microprocessor, so as to provide output signals that indicate the presence or absence of insects in the structure. If most or all of the transceivers receive positive signals indicative of the possible presence of insects in the structure, which is a false indication of the presence of insects, the microprocessor distinguishes this false indication from an actual indication of the presence of insects, thereby enabling the detection of insects despite the existence of motion signals caused by non-insect motion.

62 Claims, 6 Drawing Sheets

DEVICE AND METHOD FOR DETECTING INSECTS IN STRUCTURES

CROSS-REFERENCE TO RELATED APPLICATION

The present application is a continuation-in-part application of U.S. patent application Ser. No. 09/873,118, filed Jun. 1, 2001 now abandoned.

FIELD OF THE INVENTION

The present invention relates to a device and method for detecting insects in a structure and, more particularly, to a device and method for nondestructive testing of wood and wooden structures for the presence of wood destroying insects using microwave radiation.

BACKGROUND OF THE INVENTION

Biological attacks caused by wood destroying fungus, borers, termites, carpenter ants and the like are a major problem for structures made wholly or partially of wood. Such attacks can cause considerable damage to wooden structures.

Known methods for the damage assessment of wooden structures and detection of wood damaging insects are mostly based on visual inspection and mechanical collectors (e.g., traps) of wood destroying insects. There are a few patents that discuss using the acoustic emissions from the insects to detect the insects, but there is no evidence of successful implementation of this technique in practice. In fact, only visual inspection is currently performed to detect damage. In most cases, the visual inspection detects only damage, not the presence of the insects. Such inspection is limited only to assessable parts of the structure. As a result, most of the structure is not inspected. Moreover, even if the damage was visually detected and the structure was treated, there is no means to ensure the effectiveness of the treatment, since there is no means of determining the presence of the still living insects in the structure. Similarly, there is no known effective method for evaluating damage caused by wood destroying insects other than the visual inspection thereof.

In addition, there is no known insect detection device that is able to distinguish motion signals indicative of the presence of insects in a structure and signals caused by movement of the device itself. Since electronic insect detection devices typically contain sensitive components designed to detect the movement of insects, any movement of these devices can lead to the false indication of the presence of insects in a structure. For instance, hand tremors of an operator holding an insect detection device cause significant movement thereof. In addition, if an insect detection device is placed against a structure to be tested, structural vibrations caused by wind, appliances or nearby moving vehicles can lead to the movement of the insect detection device. Also, moving vehicles and people that pass behind a structure undergoing testing can cause motion signals that can lead to false indications of the presence of insects in a structure. As a result, it would be difficult for an operator of an insect detection device to distinguish false indications of the presence of insects in a structure from the actual presence of insects therein. Consequently, this could lead to increased time and costs for testing a structure and/or inaccurate test results.

U.S. Pat. No. 3,754,254 to Jinman (the "Jinman '254 Patent) discloses a device for detecting moving targets by the doppler shift of radiation reflected or scattered by a target that is illuminated by transmitted radiation. The Jinman '254 Patent focused on the problem of an interfering signal having a frequency difference from the transmitted radiation lying in the range of the expected doppler shift, which would give a false target indication. The Jinman '254 Patent discloses that modulating the frequency of the transmitted radiation can mitigate such problem, so that the scattered or reflected radiation has a coherence with the transmitted radiation. The Jinman '254 Patent further discloses that a device performing the aforesaid function is particularly applicable to intruder alarm systems.

U.S. Pat. No. 6,313,643 to Tirkel (the "Tirkel '643 Patent") has been distinguished from the invention disclosed by the Jinman '254 Patent on the basis that the termite detection system disclosed therein includes a transmitter adapted to transmit a "near field" microwave signal into a structure and a receiver adapted to receive reflected signals that are indicative of the presence of insects in the "near field" of the microwave signal. However, the Tirkel '643 Patent does not disclose that the termite detection system is able to detect the presence of termites within the "far field" of the signal generated thereby. As a result, the termite detection system's function is substantially constrained. In addition, the Tirkel '643 Patent does not disclose whether the termite detection system is able to distinguish output signals indicative of the presence of termites in a structure and output signals caused by movement of the termite detection system itself. As a result, it would be difficult for an operator of the termite detection system disclosed by the Tirkel '643 Patent to distinguish false indications of the presence of insects in a structure from the actual presence of insects therein and, therefore, could lead to increased time and costs for testing a structure and/or inaccurate test results.

Accordingly, what would be desirable, but has not yet been developed, is a reliable device and method for detecting the presence of wood destroying insects in wood and wooden structures.

SUMMARY OF THE INVENTION

In accordance with the present invention, an insect detection device and method employ a plurality of transceivers, each of which generates separate and distinct microwave signals and receives separate and distinct signals reflected from a structure being tested for insects. The reflected signals received by each of the transceivers are processed, for instance by a microprocessor, so as to provide output signals that indicate the presence or absence of insects in the structure being tested.

By providing a plurality of transceivers, the present invention allows a user to distinguish between false indications of the presence of insects in a structure and the actual presence of insects therein. Since most insects, such as termites, ants, etc., move along narrow paths, only one or a couple of the transceivers will detect the insects' motion, while the remaining transceivers will not detect such motion. If a condition that would trigger a false indication of the presence of insects in a structure occurs, such as hand tremors, structural vibrations, objects passing behind the structure being tested, etc. (i.e., non-insect motion), all, or substantially all, of the transceivers will receive a positive signal indicative of the presence of insects in the structure. In this case, the microprocessor's algorithm enables the detection of insects in the structure being tested despite the existence of motion signals caused by such non-insect motion, whereby false and actual indications of the presence of insects in the structure being tested can be distinguished from each other.

In accordance with other aspects of the present invention, each of the transceivers is provided with an antenna adapted to transmit microwave signals generated by its corresponding transceiver and to receive the reflected signals to be received by its corresponding transceiver. In use, each of the transceivers and its corresponding antenna are positioned a preselected distance from the portion of the structure being tested. The distance is specifically selected such that the portion of the structure being tested lies within each of the antennas' far field.

In addition, the device is provided with partitions that shield the antennas from each other, thereby reducing any interference between the microwave signals transmitted by the antennas and between the reflected signals received thereby. The partitions also shield the antennas from signals that are reflected by portions of the structure that are not, at that particular time, subject to testing, as well as from signals generated by extraneous sources such as television stations and radars. Finally, the device is provided with a demultiplexer that sequentially activates and sequentially deactivates the transceivers such that the transceivers are activated and deactivated in succession. In this regard, only one of the transceivers generates microwave signals and receives reflected signals from the structure at a particular time.

Specifically, the present invention has been adapted for use in detecting wood boring insects, such as termites, ants, etc., in wood and wooden structures. However, the present invention can be utilized to detect other insects and/or used to test structures made from materials other than wood.

Further features and advantages of the invention will appear more clearly on a reading of the detailed description of the exemplary embodiments of the invention, which are given below by way of example only with reference to the accompanying drawings.

BRIEF DESCRIPTION OF THE DRAWINGS

For a better understanding of the present invention, reference is made to the following detailed description of the exemplary embodiments considered in conjunction with the accompanying drawings, in which.

DETAILED DESCRIPTION OF THE DRAWINGS

The present invention relates to a device and method for nondestructive testing and evaluation of wood and wooden structures for degradation and damage using microwave radiation. By wooden structures it is meant any structure made wholly or partially of wood, including, but not limited to, houses, buildings, bridges, other wooden structures, wooden frames, utility poles, piles, etc. Degradation and damage may be due to biological attack, such as fungus, borers, termites, or other insects. Degradation, damage and/or other deterioration are collectively referred to herein as "damage." Detection of wood destroying insects is based on the conductivity and constant motion of the insects. Insects are comprised of electrolyte (conductive) material while wood is dielectric. This creates high contrast reflectivity for microwave radiation. Also, insects are living organisms in constant motion. The present invention detects very small movements (fraction of mm per second), thus allowing for detection of living (moving) organisms in static material. Damage evaluation is based on changes to the dielectric properties of wood caused by damage thereto such as by biological attacks.

Figure 1:
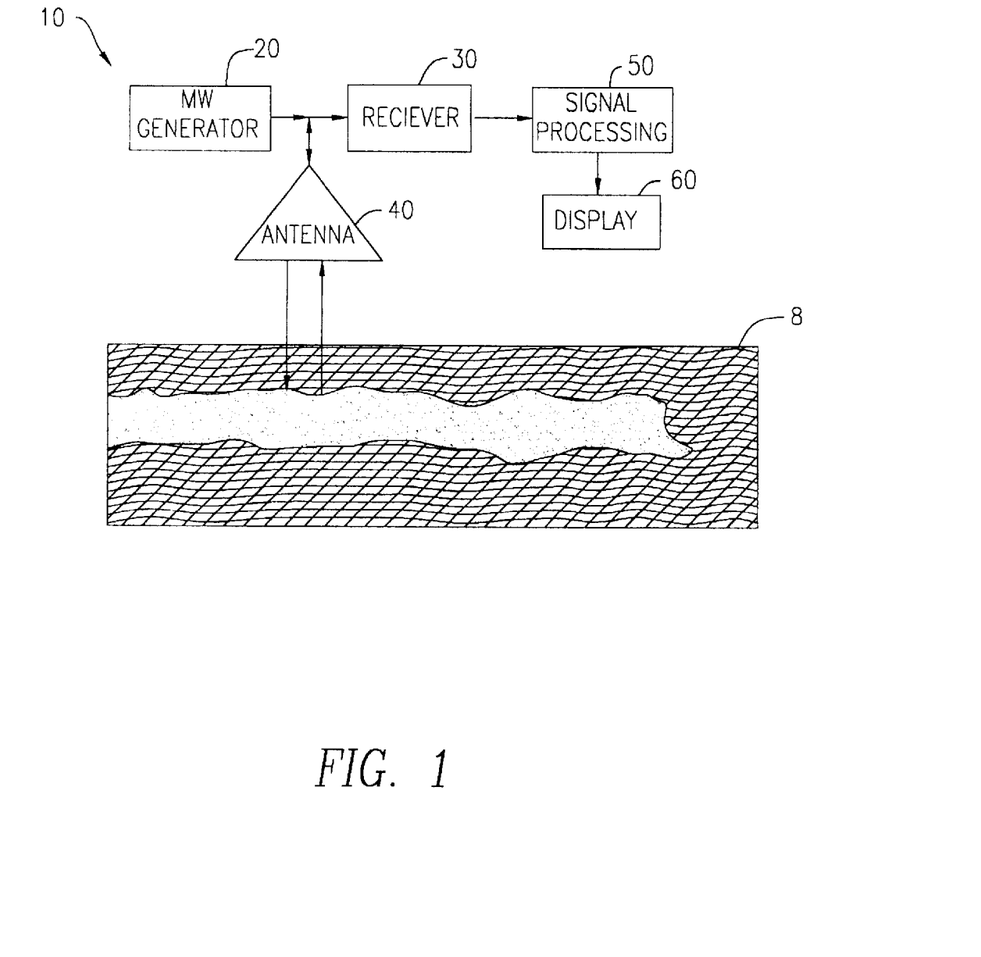
FIG. 1 is a block diagram of an insect and damage detection device in accordance with an exemplary embodiment of the present invention.

As can be seen in FIG. 1, the apparatus of the present invention, generally indicated as 10, includes a microwave generator 20, a receiver 30, an antenna 40 for sending and receiving signals, a signal processor 50 for processing the received signals and a display 60. Preferably, the apparatus is hand-held and is moved along the wooden structure 8 being tested. Microwave signals (i.e., radiation) are generated by the generator 20. The generator 20 does not have to be particularly strong; in testing it was found that a 10 mW generator was sufficient. The generated signal is constantly sent by the antenna 40, which also constantly receives a reflected signal. The signals are received by the receiver 30 and processed by the signal processor 50. Optionally, the apparatus 10 can include the display 60 for displaying the results. Alternatively, the apparatus 10 could merely emit an audio or visual alarm indicating the presence of insects.

The method includes generating and sending a microwave signal, receiving a reflected signal, and processing and evaluating the received signal. It has been found that a generated signal having a frequency of between 0.5 and 50 Ghz is suitable. The method could be employed with a hand-held unit wherein the unit is moved about a structure to be tested. Alternatively, the apparatus could be stationary and allowed to operate for a given time to cover a given area. In such a case, the apparatus could be attached to the wooden structure being tested for a short period of time, or left attached for a longer time for long term monitoring.

The apparatus 10 could additionally include a stimulator for stimulating insect movement to make detection easier (not shown in FIG. 1). The stimulator could be based on vibration, ultrasound, electromagnetic radiation, heating, etc. Preferably, a stimulator would be used prior to or during the application of the microwave probe.

An exemplary application of the invention was conducted. In the example, tests were performed with live ants contained within a plastic box and dead ants which were attached to an adhesive. The ants were placed beneath a wooden board.

Figure 2:
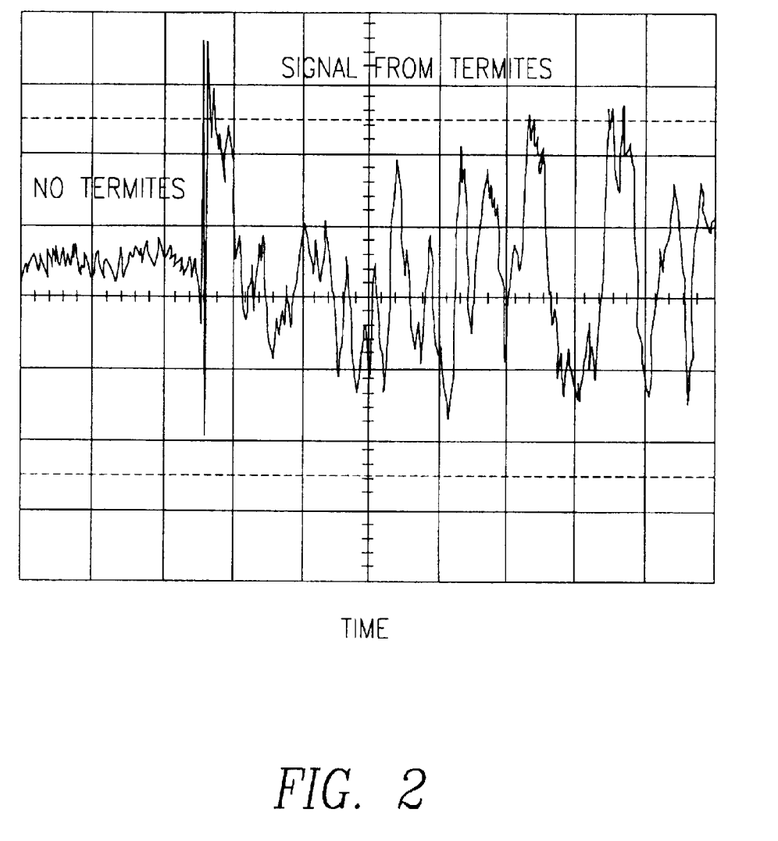
FIG. 2 is a graph of an output signal of the insect and damage detection device shown in FIG. 2, which shows both the absence and presence of live insects.

As shown in FIG. 2, where there is no motion, i.e. dead ants, there is basically no output signal from the probe. However, slight motion of live insects resulted in appreciable output signals.

In another exemplary case, live termites were put into a plastic container and one-inch wood board was used to separate the probe from the container. A significant output, similar to that shown in FIG. 2 (but not shown in the Figures), was achieved for live termites as opposed to the absence of termites.

Figure 3:
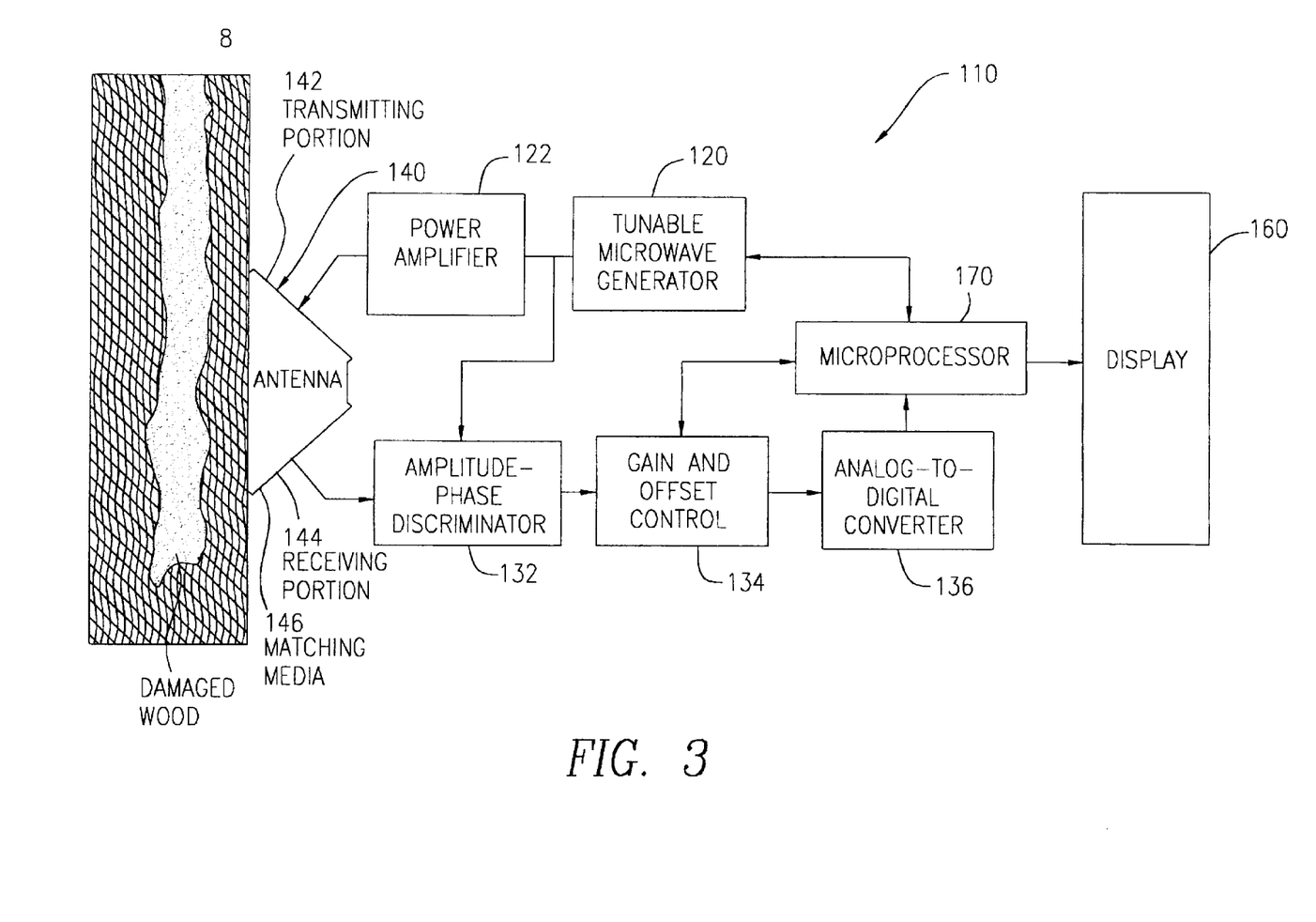
FIG. 3 is a block diagram of an insect and damage detection device in accordance with a second exemplary embodiment of the present invention.

FIG. 3 shows another embodiment of the present invention generally indicated as 110. The device includes an antenna 140 having a transmitting portion 142 and a receiving portion 144. The transmitting and receiving portions 142, 144 can be interconnected with a circulator (not shown in FIG. 3). Alternatively, two separate transmitting and receiving antennas can be utilized. The transmitting portion 142 of the antenna 140 radiates the tested wooden structure 8 with probing microwave energy. The microwaves penetrate into the tested wooden structure 8 via matching media 146 having similar properties to wood dielectric properties. Inhomogeneties in the wood, such as damage and conductive insects, cause reflection of the probing signal back to the receiving portion 144 of antenna 140. The received signal is processed for damage evaluation and moving insect detection. A tunable microwave generator 120 is controlled by a microprocessor 170. The tunable microwave generator 120 interconnects with a power amplifier 122 to deliver a signal to the antenna 140. The receiving portion 144 of antenna 140 outputs a signal to an amplitude and phase discriminator 132 that is interconnected with the tunable microwave generator 120. The signal is then sent to a gain and offset control 134 which is interconnected with the microprocessor 170 and then sent to an analog-to-digital converter 136 and then to the microprocessor 170. Finally, the output is displayed on a display 160.

In the damage evaluation mode, the microprocessor 170 sweeps the frequency range of the generator 120 to find a frequency with maximum (strongest) received signal. The antenna 140 is basically coupled to the wood and the received signal depends on the dielectric properties of the wood. Because damage to wood changes the dielectric properties of wood, the frequency deviation from a precalibrated value (which is determined using undamaged wood) indicates the presence and magnitude of damage in the structure 8. The greater the deviation, the greater the damage.

In the detection mode, the microprocessor 170 sets the fixed frequency of the generator 120. This frequency corresponds to the maximum received signal, for greatest sensitivity. If there are moving reflectors (i.e., insects) the received signal contains amplitude and phase variations due to the motion. These variations are extracted with the amplitude-phase discriminator 132 and sent to the gain and offset control device 134, which adjusts amplification and offset voltage for optimum evaluation of the signal sent to the microprocessor 170. The microprocessor 170 calculates the standard deviation of the received signal. When deviation exceeds a threshold level, predetermined during sensor calibration, the microprocessor 170 sends a live insect message to the display 160. The display can be a simple indicator, i.e. a red, green indicator, a sound indicator, or a more sophisticated LED or LCD display.

By evaluating damage and detecting insects, the present invention provides an integrated approach with built in confirmation. For example, if there is a modest indication of insect presence, the presence of damage serves to confirm that insects are present. Similarly, sweeping the frequency for damage evaluation to find the maximum received signal allows for subsequent insect detection at the frequency having maximum sensitivity. Further detecting insects after finding damage serves to confirm damage.

Figure 4:
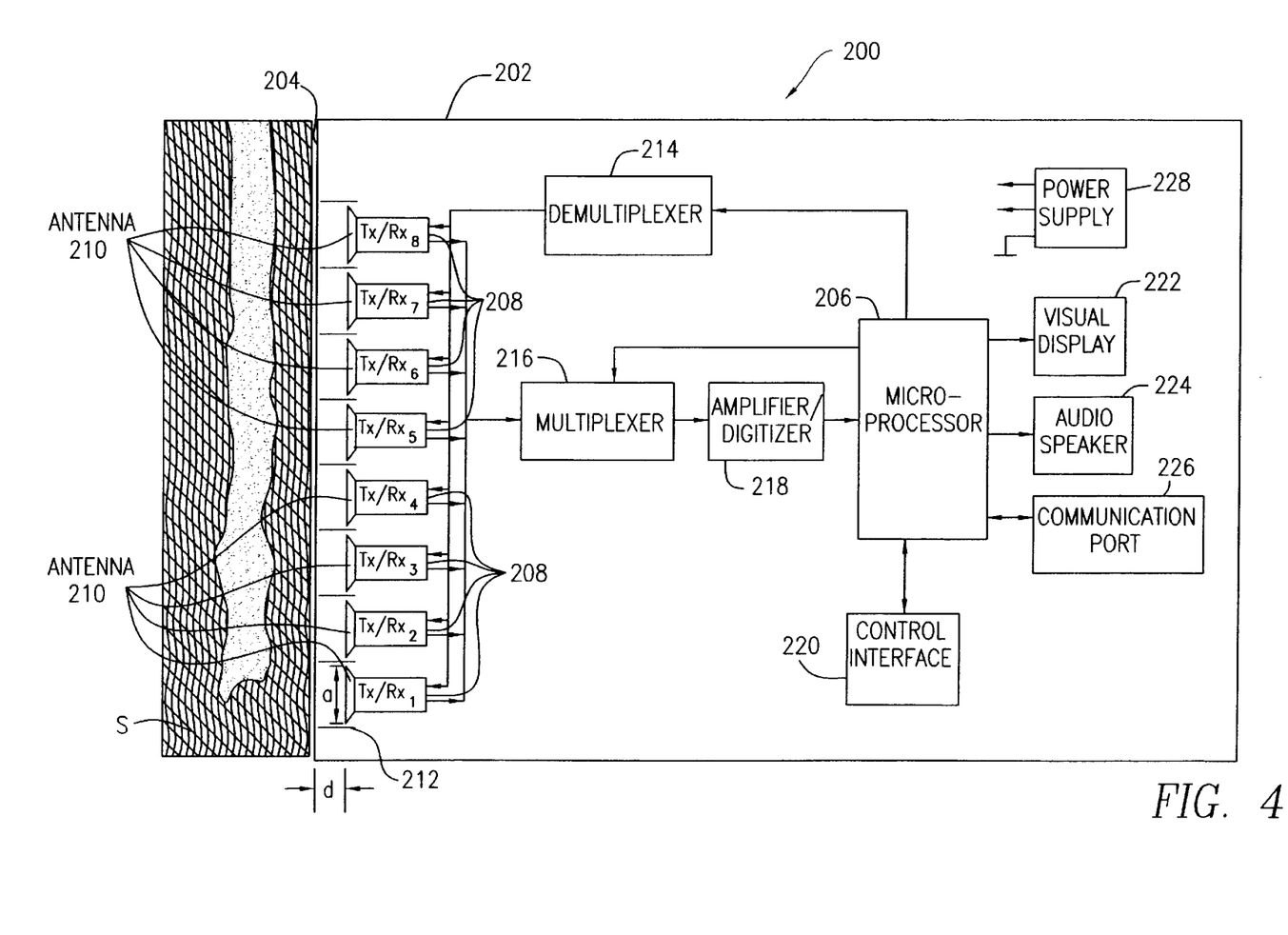
FIG. 4 is a block diagram of an insect and damage detection device in accordance with a third exemplary embodiment of the present invention.

Another exemplary embodiment of the present invention is illustrated in FIG. 4, wherein an insect detection device 200 includes a rectangular-shaped housing 202 having an end 204, a microprocessor 206 and eight (8) microwave transceivers 208 that are positioned proximate to the end 204 of the housing 202. The housing 202 supports and houses the other components of the insect detection device 200, and is preferably rectangular in shape, but it can consist of other shapes and sizes. The insect detection device 200 preferably includes the eight transceivers 208, but it may include a greater or lesser number than eight. Furthermore, the transceivers 208 are preferably positioned linearly proximate to the end 204 of the housing 202 (as shown in FIG. 4), but other configurations of the positioning of the transceivers 208 may be utilized. The transceivers 208 are sometimes collectively referred to herein as "channels" and each individually as a "channel." The functions of the microprocessor 206 and the transceivers 208 shall be described hereinafter.

Still referring to FIG. 4, each of the transceivers 208 has a corresponding horn antenna 210 connected thereto and whose function shall be described hereinafter. Each of the antennas 210 is located at a specifically selected distance "d" from the end 204 of the housing 202 (as shown in FIG. 4), whereby the distance "d" is greater than the "near field" of the signals transmitted by the antenna 210. The near field of the signal transmitted by each of the antennas 210 is defined as a distance equal to or lesser than twice the square of its aperture width divided by the wavelength of the signal transmitted thereby, i.e., near field $\leq 2a^2/\lambda$, whereby "a" is the aperture width of the antenna 210 (as shown in FIG. 4) and $\lambda$ is the wavelength of its transmitted signal. Each of the antennas 210 is preferably a horn antenna, but any or all of the antennas 210 can consist of a microstrip antenna, a dish antenna, or any other type of suitable antenna. Each of the antennas 210 and its corresponding transceiver 208 are flanked by rectangular-shaped partitions 212 (only one of which is labeled in FIG. 4 with reference number 212) whose functions shall be described hereinafter. Each of the partitions 212 is preferably rectangular in shape and manufactured from a conductive material such as aluminum, but they can consist of other shapes and sizes and/or manufactured from other materials. The insect detection device 200 can include a rectangular-shaped covering (not shown in FIG. 4), preferably manufactured from a conductive material such as aluminum, that covers the top of the partitions 212, and which, together with the partitions 212, substantially enclose each of the antennas 210.

Still referring to FIG. 4, the insect detection device 200 further includes a demultiplexer 214 and a multiplexer 216, each of which are electrically connected to and controlled by the microprocessor 206 and whose functions shall be described hereinafter. The transceivers 208 are electrically connected to the demultiplexer 214 in parallel. Similarly, the transceivers 208 are electrically connected to the multiplexer 216 in parallel. The insect detection device 200 further includes an amplifier/digitizer 218 that is electrically connected to the multiplexer 216 and the microprocessor 206 and whose function shall be described hereinafter. A control interface 220, a visual display 222, an audio speaker 224 and a communication port 226 are each electrically connected to the microprocessor 206, and the functions of which shall be described hereinafter. A power supply 228 provides electrical power to all of the aforesaid electronic components of the insect detection device 200.

It is noteworthy that the microprocessor 206 is preferably manufactured by Amtel Corporation and having a model number of ATMega-16AC, while each of the transceivers 208 is preferably manufactured by Microwave Device Technology Corporation and has a model number of MO9061. In addition, each of the antennas 210 is preferably manufactured by Microwave Device Technology Corporation and has a model number of MHA4137. The demultiplexer 214 and multiplexer 216 are each preferably manufactured by Texas Instruments, each having a model number of CD4051. Alternatively, the aforesaid components may be manufactured by other entities and/or different models of such components may be utilized.

Still referring to FIG. 4, the insect detection device 200 operates in the following manner. Each of the transceivers 208 generates microwave signals that are separate and distinct from the microwave signals generated by each of the other transceivers 208. The microwave signals generated by each transceiver 208 are transmitted by its corresponding antenna 210 into a portion of a structure S to be tested (as shown in FIG. 4) such as a wall, ceiling or floor. Each of the antennas 210 and, in turn, its corresponding transceiver 208, receives reflected signals from the structure S. The reflected signals received by each of the antennas 210 and its corresponding transceiver 208 are separate and distinct from the reflected signals received by each of the other antennas 210 and its corresponding transceiver 208. It is preferable that each of the transceivers 208 has a single corresponding antenna 210 connected thereto that both transmits microwave signals generated by the transceiver 208 and receives reflected signals to be received by the transceiver 208. Alternatively, each of the transceivers 208 may have a pair of corresponding antennas connected thereto, whereby one antenna transmits the microwave signals generated by the transceiver 208, while the other antenna receives the reflected signals to be received by the transceiver 208.

The microwave signal generated by each of the transceivers 208 is not required to be powerful. For example, a 10 mW microwave signal having a frequency within the range of 0.5 to 50 GHz is sufficient for the operation of the insect detection device 200. However, microwave signals generated by different levels of power and/or having different frequencies can be utilized. The demultiplexer 214, which is controlled by the microprocessor 206, sequentially activates and sequentially deactivates each of the transceivers 208, whereby the transceivers 208 are activated and deactivated in succession. In other words, only one of the transceivers 208 generates microwave signals and receives reflected signals from the structure S at a particular time. For example, the demultiplexer 214 activates one of the transceivers 208 (for instance, the transceiver 208 labeled as "Tx/Rx$_1$" in FIG. 4), which generates microwave signals and receives the reflected signals for a short period of time, while at the same time, the other seven transceivers 208 (labeled as "Tx/Rx$_2$" though "Tx/Rx$_8$" in FIG. 4) remain deactivated. Next, the demultiplexer 214 simultaneously deactivates the activated transceiver 208 (i.e., the transceiver 208 labeled as "Tx/Rx$_1$" in FIG. 4) and activates another one of the transceivers 208 (preferably the transceiver 208 that is next in line, which is labeled as "Tx/Rx$_2$" in FIG. 4), which generates microwave signals and receives reflected signals for a short period of time. During this time, the other seven transceivers 208 (labeled as "Tx/Rx$_1$" and "Tx/Rx$_3$" though "Tx/Rx$_8$" in FIG. 4) remain deactivated. The demultiplexer 214 activates and deactivates each of the transceivers 208 in succession and, thereafter, the cycle is repeated. Alternatively, all of the transceivers 208 may remain continuously activated.

Still referring to FIG. 4, the partitions 212 shield the antennas 210 from each other, thereby reducing any interference between the microwave signals transmitted by the antennas 210 and between the reflected signals received thereby. The partitions 212 also shield the antennas 210 from signals that are reflected by portions of a structure that are not, at that particular time, subject to testing. For example, if a front wall of a structure is subject to testing, signals are reflected from the front wall as well as, for instance, sidewalls of the structure. Consequently, the signals reflected from the sidewalls of the structure can cause interference with the signals reflected from the front wall of the structure, i.e., the portion of the structure subject to testing. Thus, the partitions 212 shield the antennas 210 from signals reflected from the sidewalls of the structure being tested, thereby reducing or eliminating interference with the signals reflected from the front wall of the structure. Finally, the partitions 212 shield the antennas 210 from extraneous sources of electromagnetic radiation, e.g., television stations, radars, etc. As previously noted, the insect detection device 200 can include a rectangular-shaped covering (not shown in FIG. 4), preferably manufactured from a conductive material such as aluminum, that covers the top of the partitions 212, which, together with the partitions 212, substantially enclose the antennas 210, and further shields the antennas 210 from each other, from signals that are reflected by portions of a structure that are not, at that particular time, subject to testing and from signals generated by extraneous sources.

The multiplexer 216, which is controlled by the microprocessor 206, receives and interrogates the reflected signals received by each of the transceivers 208. The reflected signals received by the multiplexer 216 are then amplified and digitized by the amplifier/digitizer 218, which allows for the reflected signals' data to be processed and analyzed by the microprocessor 206 in order to provide output signals that indicate the presence or absence of insects in the structure S.

When moving insects, such as termites or ants, are present in the structure S, their motion causes low frequency modulation of the reflected signals received by each of the antennas 210 its corresponding transceiver 208. The modulating frequencies of the reflected signals are typically less than 3 Hz. The modulated, reflected signals and a portion of the transmitted microwave signals are mixed within each of the transceivers 208 so as to produce low frequency difference signals, which are indicative of insect motion. It is noteworthy that because each of the antennas 210 is located at a specifically selected distance (shown in FIG. 4 as "d") that is greater than the near field of the microwave signals transmitted thereby, the structure S (and, thus, the presence of any insects therein) is located within the far field of the antennas 210.

The reflected signals are non-deterministic, that is, the output signals processed therefrom would be visualized as "noise." As a result, conventional signal processing techniques such as Fourier transforms or adaptive filtering are not very useful. Since the modulated frequency of the reflected signals (when insects are present in the structure being tested) are typically less than 3 Hz, the reflected signals received by each of the transceivers 208 are sampled at a rate greater than 3 Hz, for example 256 Hz. The acquisition time "τ" to acquire a data sample for a channel (i.e., a single transceiver 208) is preferably less than or equal to $1/(N \times F)$, where N is the number of channels (i.e., the number of transceivers 208) and F is the sampling rate in Hz. The reflected signals received by each channel is subsequently interrogated by the multiplexer 216 to produce data sample streams $D_n$ ($d_{nm}$), where "n" is a channel number, "m" is a sample number and "d" is a single bit of data.

Accordingly, the data processing and analysis conducted by the microprocessor 206 consists of calculating the moving average for each data stream $D_n$ and determination of the signal deviation indicative of a positive motion signal. The deviation could be determined by the differentiation, the calculation of signal dispersion and other similar procedures known on the art of signal processing. The deviation is compared with a predetermined threshold. If the deviation exceeds the predetermined threshold, then the audio speaker 224 will issue an audible alarm. The greater the movement of insects, the greater the deviation and the higher the pitch of the sound generated by the audio speaker 224.

Very often, however, the signal deviation could be caused by motion of the insect detection device 200 itself. For instance, hand tremors of an operator holding the insect detection device 200 while testing the structure S, structural vibrations (caused by wind, appliances, etc.) or moving vehicles and people passing behind the structure S could cause motion signals, thereby resulting in a signal deviation that exceeds the predetermined threshold. This would lead to the false indication of the presence of insects in the structure S, i.e., non-insect motion, and, consequently, "false alarms" produced by the audio speaker 224 could occur. In this regard, the plurality of transceivers 208 plays a fundamental role to discriminate between the false indication of the presence of insects in the structure S (i.e., non-insect motion) and the actual presence of insects in the structure S. Since most insects, such as termites, ants, etc. move along narrow paths, only one or a couple of the transceivers 208 will detect the insects' motion, while the remaining transceivers 208 will not detect the insects' motion. If a condition that would trigger a false indication of the presence of insects in the structure S occurs (i.e., hand tremors, structural vibrations, moving vehicles or people, etc.), all, or substantially all, of the transceivers 208 will receive a positive motion signal that indicates the possible presence of insects in the structure S, which is a false indication of the presence of insects in the structure S.

The microprocessor's 206 signal-processing algorithm is written to take into account the occurrence a false indication of the presence of insects in a structure. For example, if all or most of the transceivers 208 receive a positive signal (i.e., a motion signal) that indicates the possible presence of insects in the structure S, the microprocessor 206 will process these positive signals to determine whether they are substantially similar to each other. If the positive signals (i.e., motion signals) are substantially similar to each other, then the microprocessor 206 will extract the common positive signal received by the transceivers 208 and subtract such common positive signal from all of the signals received by the transceivers 208, thereby generating residual signals. The residual signals are then analyzed to determine the presence of insects. Therefore, the insect detection device 200 is able to detect the presence of insects in the structure S despite the existence of motion signals caused by non-insect motion.

In order to eliminate movement caused by hand tremors, the insect detection device 200 may be mounted to a stabilizing device such as a photographer's tripod, monopod or a similar mounting and stabilizing device (not shown in the Figures). Alternatively, the insect detection device 200 can be slidably mounted to a linear bearing slide and rail device, such as that manufactured by 80/20, Inc. of Columbia City, Ind. (not shown in the Figures). This type of slide and rail device can be temporarily attached to a wall by, for instance, the use of suction cups. Such a configuration would allow a user to linearly move the insect detection device 200 along the structure S being tested and take several readings. Although it is preferable that the mounting devices described above be utilized with the insect detection device 200, other mounting and stabilizing devices and means may be employed.

The visual display 222, which is controlled by the microprocessor 206, provides for a display of the output signals and/or data indicative of the absence or presence of insects in a structure S. The visual display 222 is preferably simple LED indicators (e.g., one indicator for each channel), but other visual display means, including, but not limited to, an LCD display, are available. Alternatively, the visual display 222 need not be utilized. The control interface 220, which is controlled by the microprocessor, provides for an interface between an operator and the insect detection device 200. The control interface 220 may include, but is not limited to, a power switch, volume and sensitivity controls, and an earphone plug (not shown in FIG. 4). The communication port 226, which is controlled by the microprocessor 206, allows for the signal data processed and analyzed by the insect detection device 200 to be transferred to a personal computer or a personal digital assistant (PDA). The communication port 226 is preferably either a wired or wireless universal serial bus (USB) or an RS-232 serial port. Alternatively, other types of communication ports 226 may be utilized.

Figure 5A:
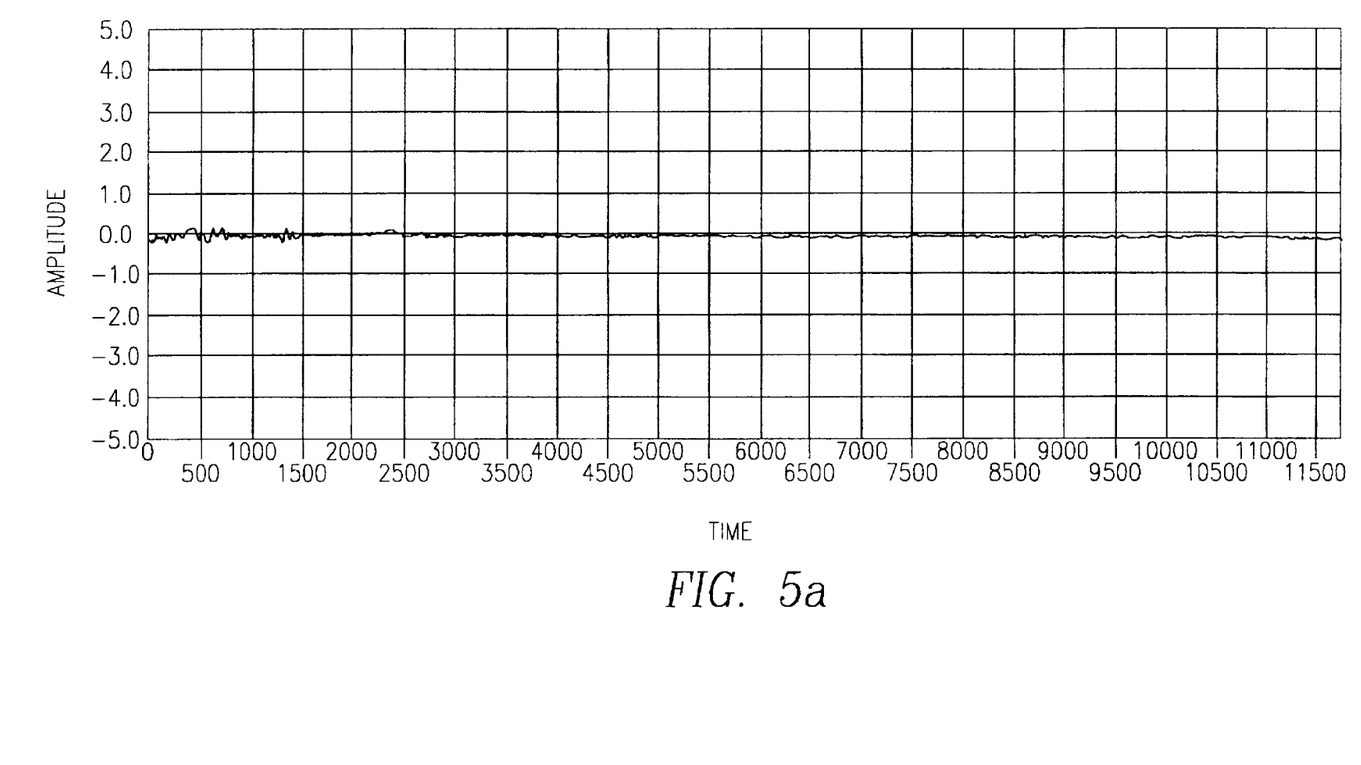
FIG. 5a is a graph of an output signal of the insect detection device shown in FIG. 4, which shows the absence of insects in a structure.
Figure 5B:
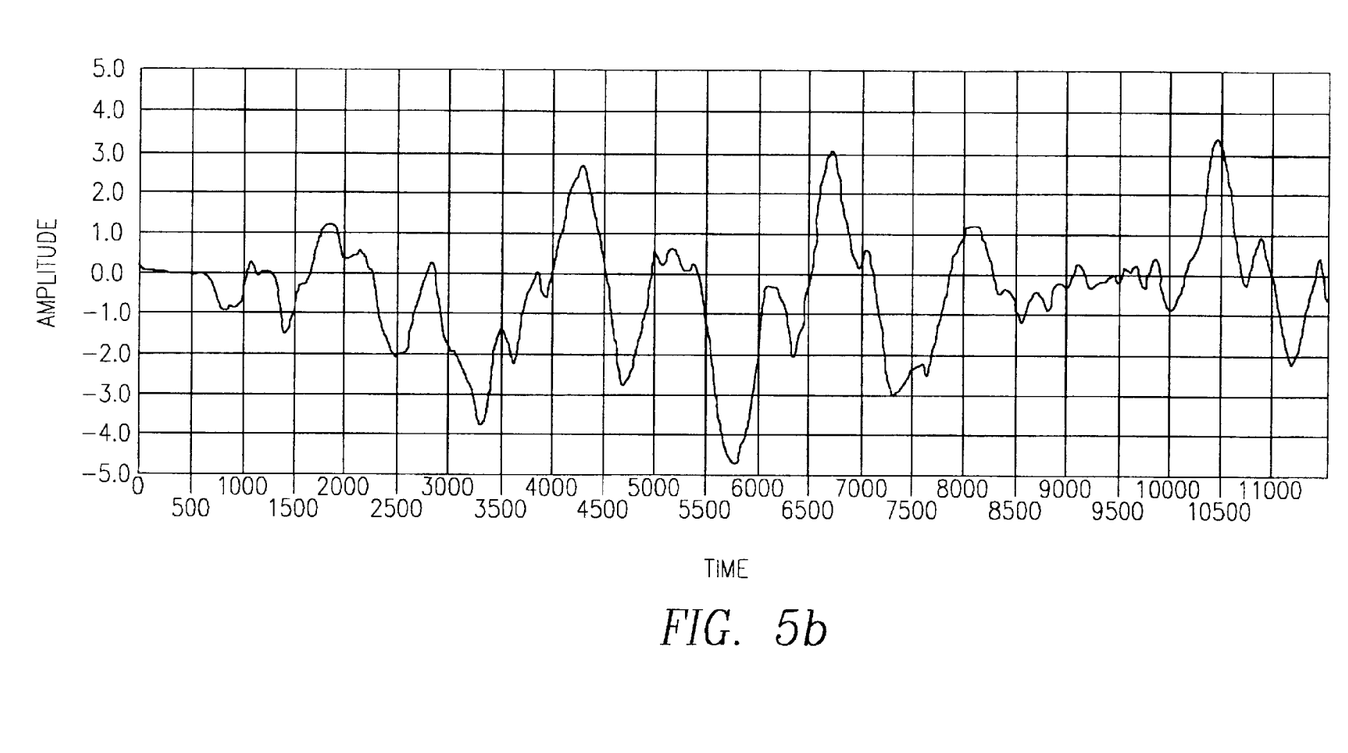
FIG. 5b is a graph of an output signal of the insect detection device shown in FIG. 4, which shows the presence of insects in a structure.

Referring to FIGS. 5a and 5b, an experimental application of the insect detection device 200 was conducted at a residence infested with live termites. The aperture width of each of the antennas 210 was 12.25 mm, while the frequency of each signal generated by each of the transceivers 208 and transmitted by each of the antennas 210 was 24.5 GHz. Therefore, the near field of the signals transmitted by each of the antennas 210 is calculated as approximately 25 mm. The insect detection device 200 was positioned approximately 30 mm from a wall of the residence, which is clearly outside the near field of the signals transmitted by the antennas 210. A portion of the wall that was known not to contain termites was first tested. In the absence of termites, the output signal generated by the insect detection device 200 has virtually no amplitude, as shown in FIG. 5a. Next, a portion of the wall that was known to contain live termites was tested. The motion of the termites resulted in output signals having appreciable amplitudes, as shown in FIG. 5b.

The insect detection device 200 can include a stimulator for stimulating insect movement so as to promote easier detection of insects (not shown in FIG. 4). The stimulator could emit vibrations, ultrasound, heat and/or electromagnetic radiation. Preferably, the stimulator would be used prior to or during the insect detection process.

The insect detection device 200 is specifically designed to detect insects in a structure being tested by performing the following steps. First, a plurality of transceivers (such as the transceivers 208) is provided for generating microwave signals and receiving reflected signals from a portion of the structure being tested. Next, each of the transceivers is provided with an antenna (such as the antennas 210) adapted to transmit microwave signals generated by its corresponding transceiver and to receive the reflected signals to be received by its corresponding transceiver. The transceivers are then positioned a preselected distance from the portion of the structure being tested, the distance being specifically selected such that the portion of the structure being tested lies within each of the antennas' far field. Next, the transceivers are sequentially activated and sequentially deactivated such that the transceivers are activated and deactivated in succession. The reflected signals received by the transceivers are then processed (for instance, by the microprocessor 206) in order to identify a positive signal that is indicative of the possible presence of insects in the portion of the structure being tested. Finally, all of the reflected signals received by the transceivers are compared to each other in order to determine whether all, or substantially all, of the transceivers have received signals substantially similar to the positive signal to thereby indicate the false presence of insects in the portion of the structure being tested.

It should be understood that the embodiments described herein are merely exemplary and that a person skilled in the art may make many variations and modifications without departing from the spirit and scope of the invention. Accordingly, all such variations and modifications are intended to be included within the scope of the invention as defined in the appended claims.

What is claimed is:

1. A device for detecting the presence of insects in a structure, comprising:
   a plurality of transceivers, each of said plurality of transceivers generating microwave signals and receiving reflected signals from a portion of a structure being tested for the presence of insects;
   processing means for processing the reflected signals received by each of said plurality of transceivers so as to provide output signals that indicate the presence or absence of insects in the portion of the structure being tested; and
   switching means, electrically connected to said plurality of transceivers and to said processing means, for sequentially activating and deactivating said plurality of transceivers such that microwave signals generated by a corresponding one of said transceivers are reflected and then received by said corresponding one of said transceivers and not by any of the other of said transceivers.

2. The device as claimed in claim 1, wherein said plurality of transceivers is arranged linearly.

3. The device as claimed in claim 1, wherein said processing means processes the reflected signals received by said plurality of transceivers in order to identify a positive signal which is indicative of the possible presence of insects in the portion of the structure being tested and compares all of the reflected signals received by said plurality of transceivers to each other in order to determine whether substantially all of the transceivers have received signals substantially similar to said positive signal to thereby indicate the false presence of insects in the portion of the structure being tested.

4. The device as claimed in claim 3, further comprising stabilizing means for stabilizing the device during the testing of the structure in order to substantially eliminate the false presence of insects in the portion of the structure being tested.

5. The device as claimed in claim 4, wherein said stabilizing means includes mounting means for removably mounting the device to the structure being tested.

6. The device as claimed in claim 5, wherein said mounting means moves the device in a linear direction along the structure being tested.

7. The device as claimed in claim 6, wherein said mounting means includes a linear slide rail having at least one suction cup capable of being removably attached to the structure being tested.

8. The device as claimed in claim 4, wherein said stabilizing means includes a stand movably positioned proximate to the structure being tested.

9. The device as claimed in claim 8, wherein said stand includes a tripod.

10. The device as claimed in claim 8, wherein said stand includes a pod.

11. The device as claimed in claim 1, wherein said processing means includes a microprocessor.

12. The device as claimed in claim 1, further comprising a plurality of antennas, each of said plurality of antennas being connected to a corresponding one of said transceivers, each of said plurality of antennas transmitting the microwave signals generated by its said corresponding one of said transceivers, and each of said plurality of antennas receiving the reflected signals to be received by its said corresponding one of said transceivers.

13. The device as claimed in claim 12, further comprising shielding means for shielding said plurality of antennas such that said antennas are shielded from one another and from signals other than the reflected signals thereby reducing interference between the microwave signals transmitted by each of said antennas and between the reflected signals received by each of said antennas.

14. The device as claimed in claim 12, further comprising housing means for housing said plurality of transceivers, said processing means and said plurality of antennas, said antennas being mounted a preselected distance from an end of said housing means.

15. The device as claimed in claim 14, wherein said antennas have a far field, said distance being selected such that the portion of the structure being tested lies within the far field of said antennas.

16. The device as claimed in claim 1, wherein said transceivers are activated and deactivated in succession by said switching means.

17. The device as claimed in claim 1, wherein said switching means includes a demultiplexer.

18. The device as claimed in claim 1, further comprising interrogating means, electrically connected to said plurality of transceivers and to said processing means, for interrogating the reflected signals received by said plurality of transceivers.

19. The device as claimed in claim 18, wherein said interrogating means includes a multiplexer.

20. The device as claimed in claim 18, further comprising amplification means, electrically connected to said interrogating means and to said processing means, for amplifying the reflected signals received by said plurality of transceivers.

21. The device as claimed in claim 20, wherein said amplification means includes an amplifier.

22. The device as claimed in claim 18, further comprising digitizing means, electrically connected to said interrogating means and to said processing means, for digitizing the reflected signals received by said plurality of transceivers.

23. The device as claimed in claim 22, wherein said digitizing means includes a digitizer.

24. The device as claimed in claim 1, further comprising output means, electrically connected to said processing means, for generating a sensory output in response to said output signals.

25. The device as claimed in claim 24, wherein said output means includes a visual display, whereby said sensory output is visible.

26. The device as claimed in claim 24, wherein said output means includes an audio speaker, whereby said sensory output is audible.

27. The device as claimed in claim 1, further comprising transferring means, electrically connected to said processing means, for transferring said output signals to a computing device.

28. The device as claimed in claim 27, wherein said transferring means includes a communication port.

29. The device as claimed in claim 1, further comprising interfacing means, electrically connected to said processing means, so as to provide an interface between said device and a user.

30. The device as claimed in claim 29, wherein said interfacing means includes a control interface.

31. A device for detecting the presence of insects in a structure, comprising:
  a housing having an end positionable adjacent to a portion of a structure being tested for insects;
  a plurality of transceivers arranged in a linear array within said housing, each of said plurality of transceivers generating microwave signals and receiving reflected signals from the portion of the structure being tested;
  a plurality of antennas, each of said plurality of antennas being connected to a corresponding one of said transceivers each of said plurality of antennas transmitting the microwave signals generated by its said corresponding one of said transceivers, and each of said plurality of antennas receiving the reflected signals received by its said corresponding one of said transceivers, said plurality of antennas being mounted a preselected distance from said end of said housing, said distance being selected such that the portion of the structure being tested lies within a far field of said antennas;
  shielding means for shielding said plurality of antennas such that said antennas are shielded from one another and from signals other than the reflected signals, thereby reducing interference between the microwave signals transmitted by each of said antennas and between the reflected signals received by each of said antennas and signals other than the reflected signals;
  switching means, electrically connected to said plurality of transceivers, for sequentially activating said transceivers and for sequentially deactivating said transceivers, such that said transceivers are activated and deactivated in succession by said switching means and such that microwave signals generated by a corresponding one of said transceivers are reflected and then received by said corresponding one of said transceivers and not by any of the other of said transceivers; and
  processing means for processing reflected signals received by each of said plurality of transceivers so as to provide output signals that indicate the presence or absence of insects in the portion of the structure being tested.

32. A method for detecting the presence of insects in a structure, comprising the steps of:
  providing a plurality of transceivers for generating microwave signals and receiving reflected signals from a portion of a structure being tested;
  providing each of said transceivers with an antenna, each antenna being adapted to transmit the microwave signals generated by its corresponding transceiver and to receive the reflected signals to be received by its said corresponding transceiver;
  positioning said plurality of transceivers a preselected distance from the portion of the structure being tested, said distance being selected such that the portion of the structure being tested lies within a far field of said antennas;
  sequentially activating and sequentially deactivating said plurality of transceivers such that said transceivers are activated and deactivated in succession and such that microwave signals generated by corresponding one of said transceivers are reflected and then received by said corresponding one of said transceivers and not by any of the other of said transceivers;
  processing the reflected signals received by said plurality of transceivers in order to identify a positive signal which is indicative of the possible presence of insects in the portion of the structure being tested; and
  comparing all of the reflected signals received by said plurality of transceivers to each other in order to determine whether substantially all of the transceivers have received signals substantially similar to said positive signal to thereby indicate the false presence of insects in the portion of the structure being tested.

33. A device for detecting the presence of insects in a structure, comprising:
  a plurality of transceivers, each of said plurality of transceivers generating microwave signals and receiving reflected signals from a portion of a structure being tested for the presence of insects;
  a plurality of antennas, each of said plurality of antennas being connected to a corresponding one of said transceivers, each of said plurality of antennas transmitting the microwave signals generated by its said corresponding one of said transceivers, and each of said plurality of antennas receiving the reflected signals to be received by its said corresponding one of said transceivers; and
  processing means for processing the reflected signals received by each of said plurality of transceivers so as to provide output signals that indicate the presence or absence of insects in the portion of the structure being tested.

34. The device as claimed in claim 33, wherein said plurality of transceivers is arranged linearly.

35. The device as claimed in claim 33, wherein said processing means processes the reflected signals received by said plurality of transceivers in order to identify a positive signal which is indicative of the possible presence of insects in the portion of the structure being tested and compares all of the reflected signals received by said plurality of transceivers to each other in order to determine whether substantially all of the transceivers have received signals substantially similar to said positive signal to thereby indicate the false presence of insects in the portion of the structure being tested.

36. The device as claimed in claim 35, further comprising stabilizing means for stabilizing the device during the testing of the structure in order to substantially eliminate the false presence of insects in the portion of the structure being tested.

37. The device as claimed in claim 36, wherein said stabilizing means includes mounting means for removably mounting the device to the structure being tested.

38. The device as claimed in claim 37, wherein said mounting means moves the device in a linear direction along the structure being tested.

39. The device as claimed in claim 38, wherein said mounting means includes a linear slide rail having at least one suction cup capable of being removably attached to the structure being tested.

40. The device as claimed in claim 36, wherein said stabilizing means includes a stand movably positioned proximate to the structure being tested.

41. The device as claimed in claim 40, wherein said stand includes a tripod.

42. The device as claimed in claim 40, wherein said stand includes a pod.

43. The device as claimed in claim 33, wherein said processing means includes a microprocessor.

44. The device as claimed in claim 33, further comprising shielding means for shielding said plurality of antennas such that said antennas are shielded from one another and from signals other than the reflected signals thereby reducing interference between the microwave signals transmitted by each of said antennas and between the reflected signals received by each of said antennas.

45. The device as claimed in claim 44, further comprising housing means for housing said plurality of transceivers, said processing means and said plurality of antennas, said antennas being mounted a preselected distance from an end of said housing means.

46. The device as claimed in claim 45, wherein said antennas have a far field, said distance being selected such that the portion of the structure being tested lies within the far field of said antennas.

47. The device as claimed in claim 33, further comprising switching means, electrically connected to said plurality of transceivers and to said processing means, for sequentially activating said plurality of transceivers.

48. The device as claimed in claim 47, wherein said transceivers are activated and deactivated in succession by said switching means.

49. The device as claimed in claim 47, wherein said switching means includes a demultiplexer.

50. The device as claimed in claim 33, further comprising interrogating means, electrically connected to said plurality of transceivers and to said processing means, for interrogating the reflected signals received by said plurality of transceivers.

51. The device as claimed in claim 50, wherein said interrogating means includes a multiplexer.

52. The device as claimed in claim 50, further comprising amplification means, electrically connected to said interrogating means and to said processing means, for amplifying the reflected signals received by said plurality of transceivers.

53. The device as claimed in claim 52, wherein said amplification means includes an amplifier.

54. The device as claimed in claim 50, further comprising digitizing means, electrically connected to said interrogating means and to said processing means, for digitizing the reflected signals received by said plurality of transceivers.

55. The device as claimed in claim 54, wherein said digitizing means includes a digitizer.

56. The device as claimed in claim 33, further comprising output means, electrically connected to said processing means, for generating a sensory output in response to said output signals.

57. The device as claimed in claim 56, wherein said output means includes a visual display, whereby said sensory output is visible.

58. The device as claimed in claim 56, wherein said output means includes an audio speaker, whereby said sensory output is audible.

59. The device as claimed in claim 33, further comprising transferring means, electrically connected to said processing means, for transferring said output signals to a computing device.

60. The device as claimed in claim 33, wherein said transferring means includes a communication port.

61. The device as claimed in claim 33, further comprising interfacing means, electrically connected to said processing means, so as to provide an interface between said device and a user.

62. The device as claimed in claim 61, wherein said interfacing means includes a control interface.

* * * * *